(12) United States Patent
Hartung et al.

(10) Patent No.: US 10,910,094 B2
(45) Date of Patent: Feb. 2, 2021

(54) COMPUTER-BASED DIAGNOSTIC SYSTEM (71) Applicant: Siemens Healthcare GmbH, Erlangen (DE)

(72) Inventors: Andre Hartung, Erlangen (DE); Razvan Ionasec, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 108 days.

(21) Appl. No.: 16/196,387

(22) Filed: Nov. 20, 2018

(65) Prior Publication Data

US 2019/0164642 A1 May 30, 2019

(30) Foreign Application Priority Data

Nov. 24, 2017 (EP) .................................. 17203507

(51) Int. Cl.
*G06K 9/00* (2006.01)
*G16H 30/20* (2018.01)
*G16H 30/40* (2018.01)
*G06K 9/62* (2006.01)
*G16H 50/20* (2018.01)
(Continued)

(52) U.S. Cl.
CPC ............. *G16H 30/20* (2018.01); *A61B 6/032* (2013.01); *A61B 6/5217* (2013.01); *G06K 9/628* (2013.01); *G06K 9/6267* (2013.01); *G06N 3/0454* (2013.01); *G06N 3/08* (2013.01); *G06T 7/0016* (2013.01); *G06T 7/11* (2017.01); *G16H 30/40* (2018.01); *G16H 50/20* (2018.01); *G06K 2209/051* (2013.01); *G06T 2207/10081* (2013.01); *G06T 2207/20081* (2013.01); *G06T 2207/20084* (2013.01); *G06T 2207/30061* (2013.01)

(58) Field of Classification Search
CPC ..................................................... G06K 9/6268
See application file for complete search history.

(56) References Cited

U.S. PATENT DOCUMENTS 5,463,548 A 10/1995 Asada et al.
2008/0292194 A1* 11/2008 Schmidt .................... G06T 7/11
382/217
(Continued)

OTHER PUBLICATIONS

Wang et al (NPL "A two-step Convolution Neural Network based Computer-aided detection scheme for automatically segmenting adipose tissue volume depicting on CT images", Compute Methods Programs Biomed. Jun. 2017 ; 144: 97-104. doi:10.1016/j.cmpb.2017.03.017.) (Year: 2017).*

(Continued)

*Primary Examiner* — Oneal R Mistry
(74) *Attorney, Agent, or Firm* — Harness, Dickey & Pierce, P.L.C.

(57) ABSTRACT

A computer-based diagnostic system includes an image generation unit adapted to generate tomographic images of a patient's organ; a deep machine learning unit configured to process generated tomographic images of the patient's organ to classify organ regions of diseased functional tissue of the patient's organ as belonging to one of a set of abnormal image patterns using trained deep neural networks; and a clinical decision support unit adapted to process classification results of the deep machine learning unit to calculate a diagnostic result output via an interface of the clinical decision support unit.

16 Claims, 3 Drawing Sheets

(51) Int. Cl.
　　　G06N 3/04　　　(2006.01)
　　　G06T 7/11　　　(2017.01)
　　　A61B 6/03　　　(2006.01)
　　　A61B 6/00　　　(2006.01)
　　　G06N 3/08　　　(2006.01)
　　　G06T 7/00　　　(2017.01)

(56)　　　　　　　　References Cited

U.S. PATENT DOCUMENTS

| 2013/0004044 | A1* | 1/2013 | Ross | G06T 7/136 |
| | | | | 382/131 |
| 2018/0300878 | A1* | 10/2018 | Ihara | G06T 7/0014 |
| 2018/0322660 | A1* | 11/2018 | Smith | G06K 9/6267 |
| 2018/0365829 | A1* | 12/2018 | Madabhushi | G06T 7/40 |
| 2019/0026897 | A1* | 1/2019 | Wu | G06T 7/11 |
| 2019/0138888 | A1* | 5/2019 | Sekiyama | G06K 9/4628 |

OTHER PUBLICATIONS

Anthimopoulos, Marios et al. "Lung Pattern Classification for Interstitial Lung Diseases Using a Deep Convolutional Neural Network" IEEE Transactions on Medical Imaging, vol. 35, No. 5, pp. 1207-1216, May 2016 // DOI: 10.1109/TMI.2016.2535865.

Humphries, Stephen M. et al. "Idiopathic Pulmonary Fibrosis: Data-driven Textural Analysis of Extent of Fibrosis at Baseline and 15-Month Follow-up" Radiology, vol. 285, No. 1, pp. 270-278, Oct. 2017 // doi:10.1148/radiol.2017161177.

Hunninghake, Gary M. et al. "MUC5B Promoter Polymorphism and Interstitial Lung Abnormalities" The New England Journal of Medicine, vol. 368, No. 23, pp. 2192-2200, Jun. 2013 // DOI: 10.1056/NEJMoa1216076.

Wells, Athol U. "The revised ATS/ERS/JRS/ALAT diagnostic criteria for idiopathic pulmonary fibrosis (IPF)—practical implications" Respiratory Research, vol. 14, No. 1, Apr. 2013; doi: 10.1186/1465-9921-14-S1-S2.

Yang, Dong et al. "Automatic Liver Segmentation Using an Adversarial Image-to-Image Network" Medical Image Computing and Computer-Assisted Intervention—MICCAI 2017, arXiv:1707.08037 [cs.CV] // DOI: 10.1007/978-3-319-66179-7_58; ISSN 0302-9743; 2017.

Hansell, David M. et al. "CT staging and monitoring of fi brotic interstitial lung diseases in clinical practice and treatment trials: a Position Paper from the Fleischner Society" The Lancet. Respiratory medicine, vol. 3, No. 6, pp. 483-496, DOI: 10.1016/S2213-2600(15)00096-X.

Jacob, Joseph et al. "Automated Quantitative Computed Tomography Versus Visual Computed Tomography Scoring in Idiopathic Pulmonary Fibrosis: Validation Against Pulmonary Function"; in Journal of Thoracic Imaging, vol. 31, No. 5, Sep. 2016, doi: 10.1097/RTI.0000000000000220.

Ley, Brett et al. "Idiopathic Pulmonary Fibrosis: CT and Risk of Death" Radiology, vol. 273, No. 2, pp. 570-579, Nov. 2014 // DOI: 10.1148/radiol.14130216.

Long, Jonathan et al. "Fully Convolutional Networks for Semantic Segmentation" IEEE Conference on Computer Vision and Pattern Recognition (CVPR), 2015 // DOI: 10.1109/CVPR.2015.7298965; arXiv:1605.06211 [cs.CV].

Kalinovsky, Alexander et al. "Lung Image Segmentation Using Deep Learning Methods and Convolutional Neural Networks" XIII Int Conf. on Pattern Recognition and Information Processing, pp. 21-24, 2016, XP055473454; Retrieved from the Internet: URL:http://imlab.grid.by/data/articles/Lung Segmentation by Convolutional NN.pdf.

Shin, Hoo-Chang et al. "Deep Convolutional Neural Networks for Computer-Aided Detection: CNN Architectures, Dataset Characteristics and Transfer Learning" IEEE Transactions on Medical Imaging vol. 35, No. 5, pp. 1285-1298, 2016.

Raghu, Ganesh et al. "An official ATS/ERS/JRS/ALAT statement: idiopathic pulmonary fibrosis: evidence-based guidelines for diagnosis and management" American Journal of Respiratory and Critical Care Medicine, vol. 183, No. 6, pp. 788-824, Mar. 2011 // DOI: 10.1164/rccm.2009-040GL.

Pathak, Deepak et al. "Constrained Convolutional Neural Networks for Weakly Supervised Segmentation" ICCV 2015; arXiv:1506.03648v2 // DOI: 10.1109/ICCV.2015.209.

* cited by examiner

COMPUTER-BASED DIAGNOSTIC SYSTEM

PRIORITY STATEMENT

The present application hereby claims priority under 35 U.S.C. § 119 to European patent application number EP17203507.3 filed Nov. 24, 2017, the entire contents of which are hereby incorporated herein by reference.

FIELD

Embodiments of the invention generally relate invention relates to a computer-based diagnostic system, in particular to a computer-based diagnostic system which can be used for diagnosis of idiopathic pulmonary fibrosis (IPF) and/or interstitial lung disease (ILD) using multi-modal data-driven texture segmentation and analysis.

BACKGROUND

The diagnosis of a disease having affected an organ of a human body can be complicated and depends often on the skills and experience of the physician performing the diagnosis. For example, idiopathic pulmonary fibrosis, IPF, and/or interstitial lung disease (ILD) are diseases of the lung which can be defined as a specific form of chronic, progressive fibrosing interstitial pneumonia of unknown cause occurring primarily in older adults. Idiopathic pulmonary fibrosis and/or interstitial lung disease (ILD) are limited to the lungs of a patient and can be associated with the histopathologic and/or radiologic pattern of UIP (usual interstitial pneumonia). Idiopathic pulmonary fibrosis and/or interstitial lung disease can be determined based on the presence of a UIP pattern on high-resolution computed tomography (HRCT) images of patients having not been subjected to surgical lung biopsy. For diagnosis of idiopathic pulmonary fibrosis IPF, and/or interstitial lung disease ILD, there exists a general guideline for performing the diagnosis for physicians. The diagnostic decision depends on the determination of presence or absence of UIP patterns in HRCT images taken of the patient's lung including present, possible or inconsistent UIP patterns. However, visual identification of a UIP pattern is impaired by inter-observer variation between the observations of different physicians. Further, radiological findings are generally communicated in non-specific qualitative terms by radiologists. Further, a HRCT-based misdiagnosis can occur when less experienced radiologists perform the evaluation of the HRCT images.

SUMMARY

At least one embodiment of the present application is directed to a computer-based diagnostic system which increases the reliability of diagnostic results with respect to diseases of a patient's organ.

At least one embodiment of the present application provides a computer-based diagnostic system comprising:
  an image generation unit adapted to generate tomographic images of a patient's organ,
  a deep machine learning unit which is configured to process the generated tomographic images of the patient's organ to classify organ regions of diseased functional tissue of the patient's organ as belonging to one of a set of abnormal image patterns using trained deep neural networks, and
  a clinical decision support unit adapted to process classification results of the deep machine learning unit to calculate a diagnostic result output via an interface of the clinical decision support unit.

BRIEF DESCRIPTION OF THE DRAWINGS

In the following, possible embodiments of different aspects of the present invention are described in more detail with reference to the enclosed figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the present application provides a computer-based diagnostic system comprising:

an image generation unit adapted to generate tomographic images of a patient's organ, a deep machine learning unit which is configured to process the generated tomographic images of the patient's organ to classify organ regions of diseased functional tissue of the patient's organ as belonging to one of a set of abnormal image patterns using trained deep neural networks, and a clinical decision support unit adapted to process classification results of the deep machine learning unit to calculate a diagnostic result output via an interface of the clinical decision support unit.

In an embodiment of the computer-based diagnostic system according to the first aspect of the present invention, the deep machine learning unit comprises trained convolutional neural networks implemented on processing stages of the deep machine learning unit.

In a further embodiment of the computer-based diagnostic system according to the first aspect of the present invention, the deep machine learning unit comprises a preprocessing stage implemented by a first trained convolutional neural network adapted to provide segmentation masks of organ parts of the patient's organ.

In a further embodiment of the computer-based diagnostic system according to the first aspect of the present invention, the deep machine learning unit comprises a localization stage implemented by a second trained convolutional network adapted to localize and delineate regions of diseased functional tissue from regions of healthy tissue within segments of the patient's organ.

In a still further embodiment of the computer-based diagnostic system according to the first aspect of the present invention, the deep machine learning unit comprises a classification stage implemented by a third trained convolutional neural network adapted to classify the regions of diseased functional tissue as belonging to one of a set of predetermined image patterns.

In a still further embodiment of the computer-based diagnostic system according to the first aspect of the present invention, the convolutional neural network of the localization stage of the deep machine learning unit is a constrained convolutional neural network.

In a still further embodiment of the computer-based diagnostic system according to the first aspect of the present invention, the clinical decision support unit is adapted to process additional clinical parameters of the patient to calculate the diagnostic result.

In a still further embodiment of the computer-based diagnostic system according to the first aspect of the present invention, a sequence of tomographic images of a patient's organ taken by the image generation unit over time is processed and classified by the deep machine learning unit and evaluated to provide diagnostic results by the clinical decision support unit indicating changes and/or progression in the classification results of the respective patient.

In a still further embodiment of the computer-based diagnostic system according to the first aspect of the present invention, the image generation unit is adapted to generate a number of tomographic images each formed by an image slice of the patient's organ having a plurality of image pixels.

In a further embodiment of the computer-based diagnostic system according to the first aspect of the present invention, the classification stage of the deep machine learning unit is configured to calculate quantitative results comprising scores for the different abnormal image patterns classified by the classification stage.

In a further embodiment of the computer-based diagnostic system according to the first aspect of the present invention, a percentage score of an abnormal image pattern comprises a ratio between the number of voxels within the patient's organ region and classified as belonging to the abnormal image pattern and a total number of voxels within the patient's organ region.

In a further embodiment of the computer-based diagnostic system according to the first aspect of the present invention, the image generation unit is adapted to generate tomographic chest images of a patient's chest comprising different organs of the patient including the lung organ of the patient.

In an embodiment of the computer-based diagnostic system according to the first aspect of the present invention, the preprocessing stage of the deep machine learning unit is configured to provide segmentation masks for all lung lobs of the patient's lung organ.

In a further embodiment of the computer-based diagnostic system according to the first aspect of the present invention, the classification stage of the deep machine learning unit is configured to classify regions of diseased functional tissue as belonging to a set of predetermined image patterns including fibrosis, emphysema, honeycombing, ground glass opacity, reticular, cysts, consolidation and mosaic attenuation.

In a further embodiment of the computer-based diagnostic system according to the first aspect of the present invention, the clinical decision support unit is configured to output as a diagnostic result whether regions of the patient's lung organ are affected by idiopathic pulmonary fibrosis and/or interstitial lung disease.

Figure 1:
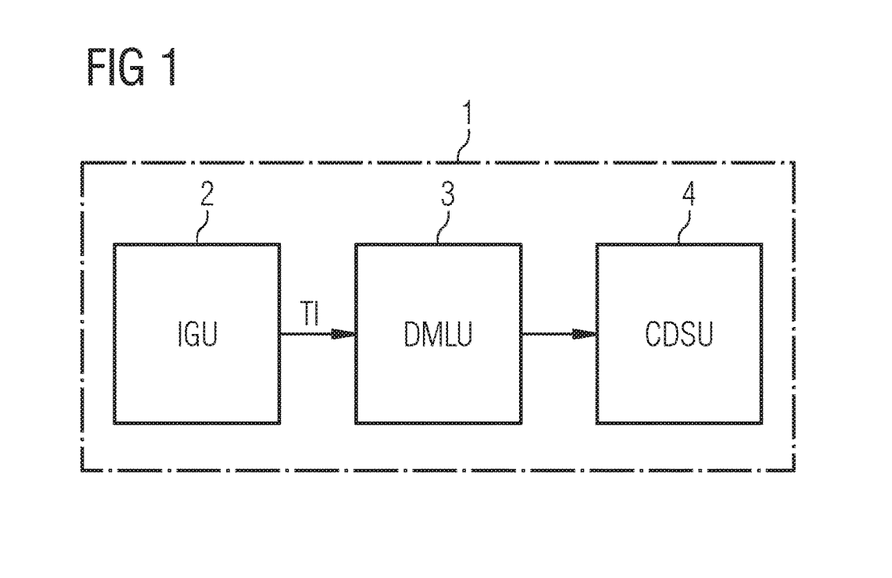
FIG. 1 shows a block diagram of an example embodiment of a computer-based diagnostic system according to the present invention.

As can be seen in the block diagram of FIG. 1, the computer-based diagnostic system 1 according to a first aspect of the present invention comprises in the illustrated embodiment three main subunits. In the illustrated embodiment, the computer-based diagnostic system 1 comprises an image generation unit 2, a deep machine learning unit 3 and a clinical decision support unit 4. The different subunits can be connected directly as illustrated in FIG. 1 or can form a distributed system connected via network links.

The image generation unit 2 is adapted to generate tomographic images of a patient's organ, in particular of the patient's lung. The image generation unit 2 can be adapted to generate a number of tomographic images each formed by an image slice of the patient's organ wherein each tomographic image can comprise a plurality of image pixels, e.g. 512 pixels×512 pixels. The tomographic images can provide image sections through the body of the patients using different kinds of penetrating waves. The image generation unit 2 can generate tomographic images TI with a high resolution.

A CT scan or computer tomography scan can make use of computer process combinations of different measurements taken from different angles to produce cross-sectional tomographic images of virtual slices of specific areas of a scanned object such as a patient's organ within a human body. Digital geometry processing can be used to generate a three-dimensional volume of the inside of the scanned object from a series of two-dimensional tomographic images taken around a single axis of rotation. A computer tomographic scan can be used for detecting both acute and chronic changes in the lung parenchyma, i.e. the internals of the patient's lungs. This is particular relevant because normal two-dimensional x-rays do not show such defects.

For evaluation of chronical interstitial processes, such as emphysema, fibrosis, etc., thin sections with high spatial frequency reconstructions can be used wherein the CT scans performed by the image generation unit 2 can be performed both in inspiration and expiration. This technique is also called high-resolution CT.

As shown in FIG. 1, the tomographic images generated by the image generation unit 2 are supplied to the deep machine learning unit 3 of the computer-based diagnostic system 1. The deep machine learning unit 3 is adapted to process the received tomographic images of the patient's organ, in particular of the patient's lung, to classify organ regions of diseased functional tissue of the patient's organ as belonging to one of a set of predetermined abnormal image patterns using trained deep neural networks, in particular trained convolutional neural networks CNNs. The deep machine learning unit 3 is adapted to classify the regions of diseased functional tissue of the patient's organ as belonging to a set of predetermined image patterns. For instance, for the patient's lung, the deep machine learning unit 3 can provide specifications of regions of the diseased functional tissue as belonging to one of a set of predetermined image patterns comprising fibrosis, emphysema, honeycombing, ground glass opacity, reticular, cysts, consolidation or mosaic attenuation.

The image patterns can comprise primary image patterns and secondary image patterns. The secondary image patterns include for instance patterns specific to pathological images (e.g. fibrosis, honeycombing) or abnormality of the right circulatory system including pulmonary artery, right ventricle dilation as well as patterns specific to other image modalities, e.g. MRI or PET. A classification processing stage of the deep machine learning unit 3 can provide quality classification results for specific organ regions but also in an embodiment quantity diagnostic results. The classification stage of the deep machine learning unit 3 is configured in an embodiment to calculate quantitative results comprising scores of the different abnormal image patterns classified by the classification stage.

In an implementation, a percentage score of an abnormal image pattern is calculated by the deep machine learning unit 3 wherein the percentage score comprises a ratio between a number of voxels within a patient's organ region specified as belonging to one of a set of predetermined abnormal image patterns and a total number of voxels within the respective patient's organ region. The deep machine learning unit 3 of the computer-based diagnostic system 1 supplies the quantitative and qualitative classification results in an embodiment to the clinical decision support unit 4 as illustrated in FIG. 1. The clinical decision support unit 4 can be a local support unit or a remote support unit connected to the output of the deep machine learning unit 3 via a data network. The clinical decision support unit 4 is configured to process the received classification results and can comprise quantitative and/or qualitative classification results to calculate a diagnostic result which can be output via a user interface and/or a data interface of the clinical decision support unit 4.

Figure 2:
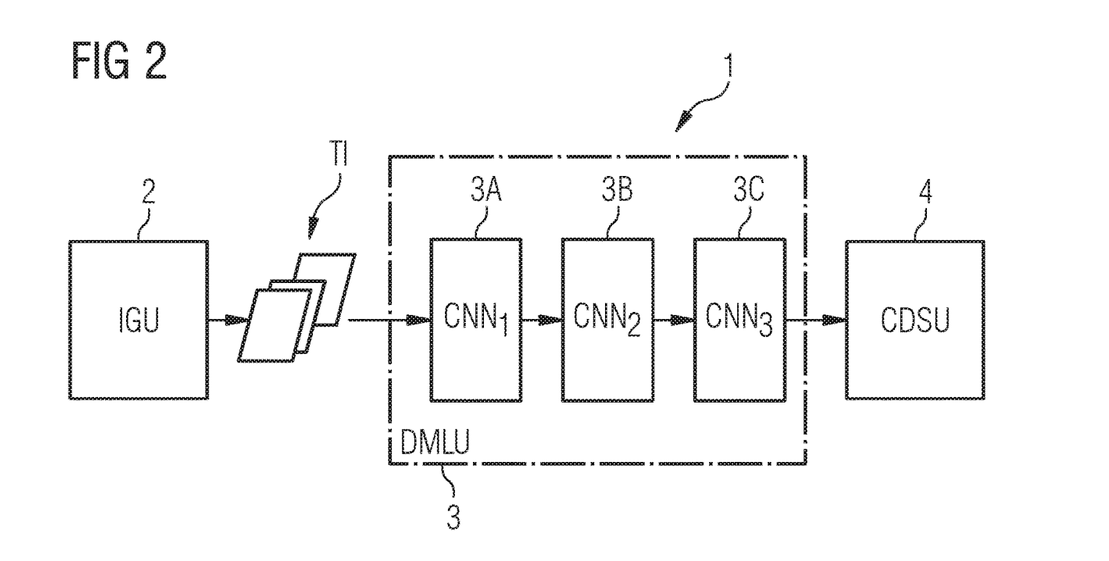
FIG. 2 shows a further block diagram for illustrating an example embodiment of a computer-based diagnostic system according to the present invention.

FIG. 2 shows a block diagram of an example embodiment of the computer-based diagnostic system 1 according to an aspect of the present invention. As can be seen in FIG. 2, an image generation unit 2 provides a number of tomographic images each comprising a plurality of pixels to a data input of the deep machine learning unit 3. The deep machine learning unit 3 processes the received tomographic images to classify regions of diseased functional tissue as belonging to one of a set of predetermined abnormal image patterns using trained deep neural networks.

The classification results are output to a clinical decision support unit 4 as shown in FIG. 2. The clinical decision support unit 4 has in an embodiment a user interface to output the calculated diagnostic results comprising qualitative diagnostic results and/or quantitative diagnostic results. In the illustrated embodiment of FIG. 2, the deep machine learning unit 3 comprises several processing stages 3A, 3B, 3C. In the illustrated embodiment of FIG. 2, the deep machine learning unit 3 comprises trained convolutional neural networks CNNs implemented on three different processing stages 3A, 3B, 3C.

The deep machine learning unit 3 comprises in the illustrated embodiment a preprocessing stage 3A implemented by a first trained convolutional neural network CNN1 to provide a segmentation mask of organ parts of the patient's organ. An end-to-end convolutional neural network CNN approach can be used to produce a segmentation mask representing the labels of lung lobs from a received tomographic image, in particular a chest image taken of a patient.

The convolutional neural network CNN of the preprocessing stage 3A can be trained using a supervised approach by utilizing pre-labeled/segmented images of the pulmonary lobs of the patient's lung. In an implementation, a fully convolutional neural network CNN can be used or an adversarial deep image-to-image network can be used to complete the preprocessing step. The data output of the preprocessing stage 3A of the deep machine learning unit 3 represents in an embodiment an automated segmentation of the lungs of the patient and its five pulmonary lobs.

The deep machine learning unit 3 comprises in the illustrated embodiment of FIG. 2 a second processing stage formed by a localization stage. The localization stage 3B is implemented in an embodiment by a second convolutional neural network CNN2 adapted to localize and delineate regions of diseased functional tissue from regions of healthy tissue within segments of the patient's organ. The localization stage 3B can delineate diseased functional organic tissue (parenchyma) from healthy organic tissue. This task can be complex due to the diffuse and heterogeneous appearance of various disease patterns. The second convolutional neural network CNN2 can be trained in an embodiment on training images comprising labels. A level of labeled information can range from information of presence or absence of a specific image to the visual quantification of the extent of a specific pattern for given organic regions, in particular lung lobs of a patient's lung.

In an embodiment, the convolutional neural network CNN of the localization stage 3B of the deep machine learning unit 3 can be formed by a constrained convolutional neural network CCNN. The constrained convolutional neural network CCNN can be used to learn to delineate diseased tissue in each organ region such as a lung lob from weakly labeled images. The output of the localization stage 3B represents an automated segmentation of regions of unspecified diseased functional organic tissue (parenchyma) of the affected patient's organ.

In the illustrated embodiment of FIG. 2, the deep machine learning unit 3 comprises as a third processing stage a classification stage 3C. In the illustrated embodiment of FIG. 2, the classification stage 3C is also implemented by a convolutional neural network CNN adapted to classify the regions of diseased functional tissue as belonging to one of a set of predetermined image patterns.

The classification stage takes as input the delineated (segmented) region of functional tissue marked as diseased and classifies in an embodiment each image pixel (or image patch) as one of the abnormal image patterns in focus such as fibrosis or emphysema, etc. The third convolutional neural network CNN3 implemented in the classification stage 3C can be trained in an embodiment on a set of annotated image patches to fulfil the classification task. Using a sliding window approach, the trained convolutional neural network CNN can be applied in an exhausted grid like sampling at each location within the delineated diseased parenchyma region.

At each location, the respective image pixel or image patch can be classified as belonging to one of a predetermined set of abnormal image patterns. After classification by the classification stage 3C, a quality qualification result can be output by the classification stage 3C to the clinical decision support unit 4. The classification stage 3C of the deep machine learning unit 3 can also be configured to calculate quantity results comprising scores of the different abnormal image patterns classified by the classification stage 3C.

The qualitative and quantitative results can for instance comprise scores, in particular percentage scores, of an abnormal image pattern comprising for instance a ratio between the number of voxels within the patient's organ region classified as belonging to the abnormal image pattern and a total number of available voxels within the patient's organ region. The quantification can be completed by counting the pixels or voxels belonging to each class to produce a percentage score. In an embodiment, the percentage scores can be computed or calculated for each lob or section of the patient's organ separately.

The computer-based diagnostic system 1 as illustrated in FIG. 2 can for instance be used to provide diagnostic results with respect to a patient's lung. In this embodiment, the image generation unit 2 can be adapted to generate tomographic chest images of the patient's chest comprising the patient's lung organ. The preprocessing stage 3A of the deep machine learning unit 3 can be configured to provide a segmentation mask for all lung lobs of the patient's lung organ. The classification stage 3C of the deep machine learning unit 3 is then configured to classify regions of diseased functional tissue as belonging to a set of predetermined image patterns including fibrosis, emphysema, honeycombing, ground glass opacity, reticular, cysts, consolidation and mosaic attenuation.

The clinical decision support unit 4 is configured to output as a diagnostic result whether regions of the patient's lung organ are affected by idiopathic pulmonary fibrosis IPF and/or interstitial lung disease ILD. Idiopathic pulmonary fibrosis IPF and/or interstitial lung disease ILD are specific forms of chronic, progressive, fibrosing interstitial pneumonia of unknown cause, occurring primarily in older adults. Pulmonary fibrosis is a respiratory disease where scars are formed in the lung tissues leading to serious breathing problems. Scar formation, i.e. the accumulation of excess fibrous connective tissue (the process called fibrosis), leads to a thickening of the walls and causes a reduced oxygen supply in the blood. Pulmonary fibrosis can appear without any known cause. In this case, it is termed "idiopathic". Idiopathic pulmonary fibrosis and/or interstitial lung disease can lead to specific characteristic image patterns within the tomographic images of the patient's lung.

The qualitative and/or quantitative classification results are output by the classification stage 3C to the clinical decision support unit 4 which can calculate a diagnostic result output to a physician via an interface. In an embodiment, the clinical decision support unit 4 can be adapted to process additional clinical parameters of the patient to calculate a corresponding diagnostic result of the respective patient. These additional clinical parameters used by the clinical decision support unit 4 can include patterns extracted from histopathology of lung biopsy, quantification of the right ventricular size and function, size of the pulmonary artery, functional parameters including genetic factors as well as personal data including gender, age or related physiology information concerning the respective patient. In an embodiment, the clinical decision support unit 4 retrieves additional parameter data from a patient database and/or receives the parameters via a user interface.

In an embodiment of the computer-based diagnostic system 1 according to the present invention, the sequence of tomographic images of a patient's organ can be generated or taken by the image generation unit 2 over time. The sequence of tomographic images can be processed and classified by the deep machine learning unit 3 and evaluated by the support unit 4 to provide diagnostic results indicating changes and/or progression in the classification results of the respective patient. The sequence of tomographic images TI can comprise a number of tomographic images, in particular chest images, taken for instance periodically in a predetermined time span. For instance, a set or group of tomographic images TI of a patient are taken every day to find changes and/or progression in the classification results.

The classification and quantification results can be used together with additional clinical parameters to provide an end-to-end differential diagnostic output. The classification of progression in stable, slow progressing and rapid progressing can be based on longitudinal, serial, images provided using the computed quantification of abnormal image patterns. In an embodiment, first, the classification and quantification is determined for each of the tomographic images TI in the time series independently. Second, in an embodiment, a rate of change for each of the image patterns can be computed as the average slope normalized by the time interval between each scan of the image generation unit 2. By considering a current measurement of progression (e.g. more than 10% drop in FVC) as a label for rapid progression and anything below as slow, and no drop as stable, a machine learning algorithm can be trained to learn the pattern parameter distribution for modeling a three-class classification problem.

In an implementation, the clinical decision support unit 4 can be configured to output as a diagnostic result to return YES, NO or PROBABLE as an output to indicate whether the patient's lung organ has been affected by idiopathic pulmonary fibrosis IPF and/or interstitial lung disease ILD. Depending on the diagnostic result output by the clinical decision support unit 4, the system 1 can give a recommendation for treating the diagnosed disease. This recommendation can include recommendations for drugs and/or necessary surgery.

The computer-based diagnostic system 1 can calculate fully automatically diagnostic results without being dependent on the skills and experience of physicians performing the diagnosis. The computer-based diagnostic system can fully automatically detect abnormality patterns (UIP patterns) being relevant for IPF disease. It further can localize the abnormality and classify as well as quantify the extent and the type of the respective localized abnormality. The computer-based diagnostic system 1 can provide additional information for the assessment of the disease such as emphysema extent being present in at least a third of IPF patients. Additionally, the computer-based diagnostic system 1 can provide qualitative and quantitative information relevant for the assessment of interstitial lung disease in general. In an embodiment, the computer-based diagnostic system 1 can also provide a score progression of disease in longitudinal CT and may contribute to the prognosis of progression as well as prediction of a treatment outcome. The computer-based diagnostic system 1 uses a hierarchical approach that allows for training with labeled data and can help to perform a texture analysis for diffused disease patterns.

Figure 3:
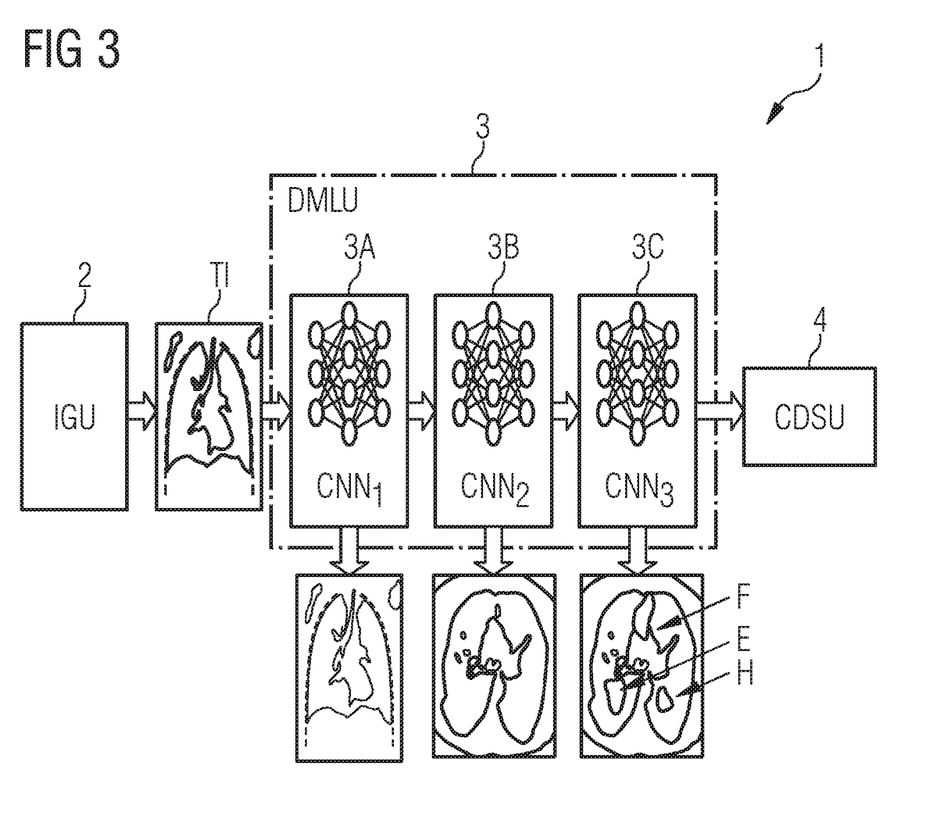
FIG. 3 shows a further diagram for illustrating an example system architecture of a computer-based diagnostic system according to an embodiment of the present invention.

FIG. 3 shows a schematic diagram for illustrating an example system architecture of a computer-based diagnostic system 1 according to an embodiment of the present invention. In the illustrated embodiment, the image generation unit 2 supplies at least one chest image slice of a patient to the deep machine learning unit 3 comprising the three processing stages 3A, 3B, 3C. The processed images output by the different processing stages of the deep machine learning unit can be temporarily memorized and used for further processing by the following processing stages.

The preprocessing stage 3A provides a segmentation mask of organ parts, in particular lung lobs of the patient as shown in FIG. 3. The localization stage 3B provides images of the different organ regions such as the five lung lobs wherein regions of diseased functional tissue are localized. The classification stage 3C can classify the regions of diseased functional tissue as belonging to one of a set of predetermined image patterns of abnormalities. In the illustrated example of FIG. 3, the regions of the diseased functional tissue of the lung are classified as belonging to a set of predetermined image patterns which are formed in the illustrated example by fibrosis F, emphysema E and honeycombing H.

In an embodiment, the classification stage can output a list of classes as a quality classification result along with a quantitative classification result comprising percentage scores of the found abnormal image patterns.

| Healthy | 79% |
|---|---|
| Fibrosis | 10% |
| Emphysema | 7% |
| Honeycombing | 3% |
| Ground Glass Opacity | 1% |
| Reticular | 0% |
| Cysts | 0% |
| Consolidation | 0% |
| Mosaic Attenuation | 0% |

The percentage score as illustrated in the given table can comprise a ratio between the number of voxels within the patient's organ region classified as belonging to the abnormal image pattern and a total number of voxels within the patient's organ region. In the given example, 79% of the tissue of the organ region has been classified as healthy. The remaining 21% are formed by tissue affected by disease. In the illustrated example, the classification stage can classify regions of the patient's organ, i.e. lung, as belonging to one of a set of predetermined abnormal image patterns including fibrosis, emphysema, honeycombing, ground glass opacity, reticular, cysts, consolidation and mosaic attenuation. For instance, 10% of the diseased functional tissue is classified as belonging to fibrosis F.

The classification result represented by the list or table can be stored temporarily for further evaluation. In an embodiment, the classification results can be calculated periodically in response to received tomographic images TI of the patient's organ. Consequently, a set of classification results for a specific organ region can be stored in a database and processed to find trends in the development of the disease. Further, the impact of drugs and/or surgery on the developing disease can be observed and analyzed.

Figure 4:
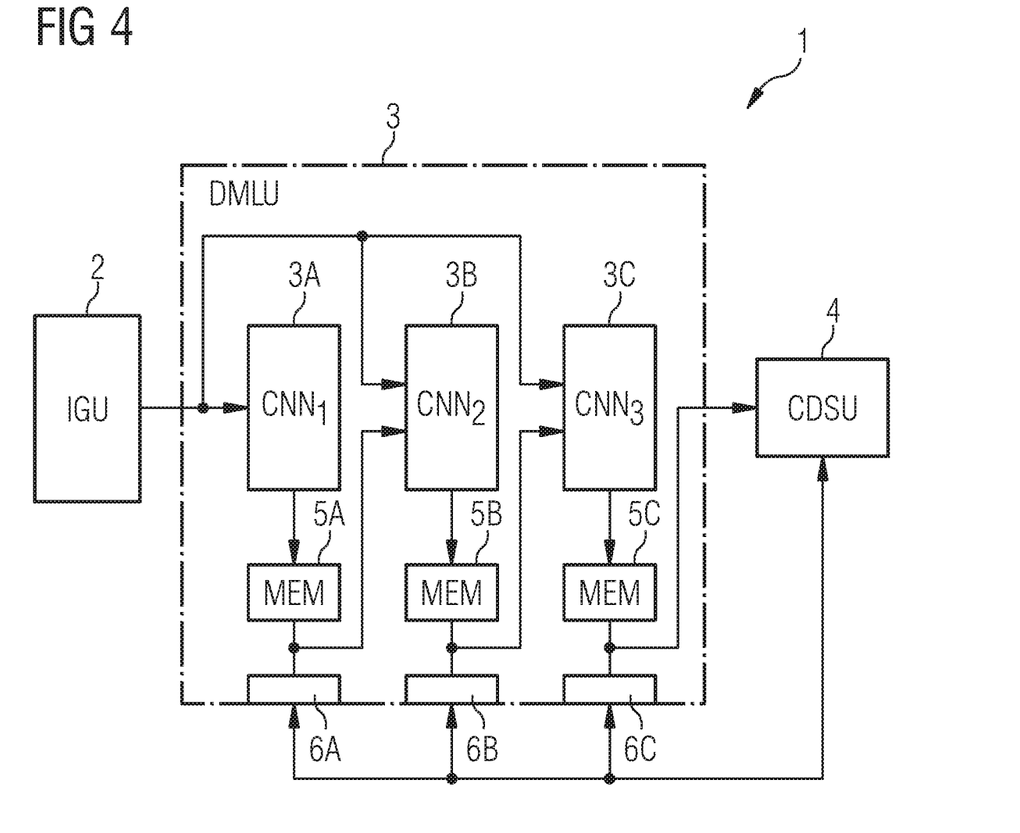
FIG. 4 shows a further schematic diagram for illustrating an example embodiment of a computer-based diagnostic system according to the present invention.

FIG. 4 shows a block diagram of a further possible example embodiment of a computer-based diagnostic system 1 according to the present invention. In the illustrated embodiment of FIG. 4, each processing stage 3A, 3B, 3C of the deep machine learning unit 3 comprises a memory 5A, 5B, 5C for storing temporarily processed output data which can be used for the following processing stage of the deep machine learning unit 3. The output of each processing stage as stored in its memory can further be supplied via a data interface 6A, 6B, 6C to the clinical decision support unit 4.

In the illustrated embodiment, the clinical decision support unit 4 can have access to the classification result of the last processing stage 3C of the deep machine learning unit 3 but also can have access to the intermediate data of the other processing stages 3A, 3B of the deep machine learning unit 3. In this embodiment, the diagnostic result can be calculated on the output data of each processing stage of the deep machine learning unit 3. Further, the tomographic images generated by the image generation unit 2 are applied to each processing stage 3A, 3B, 3C of the deep machine learning unit 3 as shown in FIG. 4.

In the illustrated embodiment of FIGS. 2, 3, 4, each processing stage of the deep machine learning unit 3 is formed by a convolutional neural network CNN. The convolutional neural network CNN comprises at least one input layer, one or several hidden layers and an output layer. The convolutional neural network CNN is a deep feed-forward artificial neural network. The convolutional neural network CNN consists of an input layer, an output layer as well as multiple hidden layers in-between. The hidden layers of the convolutional neural network CNN comprise typically convolutional layers, pooling layers, fully connected layers as well as normalization layers. The convolution is performed to extract features from the received tomographic input image. The convolution preserves the spatial relationship between pixels by learning image features using for instance small squares of input data. The system according to the present invention provides an accurate and objective quantification of individual IPF patterns including an initiation of treatment, inclusion in clinical trials and referral for lung transplantation or palliation.

The system 1 is able to identify patients with progressive fibrosis to discriminate between stable, slow progressing and rapid progressing fibrosis. Besides clinical management, the progression prognosis which can be provided by the clinical decision support unit 4 of the system 1 is also relevant for patient selection in the context of clinical trial for the avoidance of inclusion of patients with non-progressive disease in clinical trials. The computer-based diagnostic system 1 according to the present invention can address the entire spectrum of relevant image patterns relevant to IPF clinical management. The computer-based diagnostic system 1 provides diagnostic results automatically and can provide statistical data for complex patterns encountered in IPF patients.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-based diagnostic system, comprising:
   a deep machine learning unit configured to classify a region of an organ of a patient as corresponding to one of a set of abnormal image patterns based on a tomographic image of the organ using a plurality of trained convolutional neural networks (CNNs) to obtain a classification result, the set of abnormal image patterns corresponding to diseased function tissue; and
   processing circuitry configured to
     calculate a diagnostic result based on the classification result, and
     output the diagnostic result via an interface,
   wherein
     the plurality of trained CNNs correspond to a plurality of processing stages of the deep machine learning unit,
     the plurality of trained CNNs includes a first trained CNN corresponding to a localization stage among the plurality of processing stages, the first trained CNN configured to delineate a plurality of respective regions of diseased functional tissue from regions of healthy tissue within a segment of the organ, the plurality of respective regions including the region, and
     the plurality of trained CNNs includes a second trained CNN corresponding to a classification stage among the plurality of processing stages, the second trained CNN configured to classify each of the plurality of respective regions of diseased functional tissue as corresponding to a respective one of the set of abnormal image patterns.

2. The computer-based diagnostic system of claim 1, wherein the plurality of trained CNNs includes a third trained CNN corresponding to a preprocessing stage among the plurality of processing stages, the third trained CNN configured to provide a segment of the organ from the tomographic image.

3. The computer-based diagnostic system of claim 1, wherein the first trained CNN is a constrained convolutional neural network (CCNN).

4. The computer-based diagnostic system of claim 1, wherein the processing circuitry is configured to calculate the diagnostic result based on the classification result and additional clinical parameters of the patient.

5. The computer-based diagnostic system of claim 1, wherein
   the tomographic image is one in a sequence of tomographic images of the organ captured over time;
   the deep machine learning unit is configured to classify each tomographic image in the sequence of tomographic images to obtain a plurality of classification results, the plurality of classification results including the classification result; and
   the processing circuitry is configured to calculate the diagnostic result based on the plurality of classification results, the diagnostic result indicating at least one of a change, a progression, a rate of change, a prognosis or a risk classification.

6. The computer-based diagnostic system of claim 1, wherein the tomographic image is one of a plurality of tomographic images, each of the plurality of tomographic images corresponding to an image slice of the organ, and each of the plurality of tomographic images including a plurality of image pixels.

7. The computer-based diagnostic system of claim 1, wherein the deep machine learning unit is configured to calculate scores for different abnormal image patterns among the set of abnormal image patterns to which the region of the organ corresponds during the classification stage.

8. The computer-based diagnostic system of claim 7, wherein the scores for the different abnormal image patterns include a percentage score of a respective abnormal image pattern computed based on a ratio between a number of voxels of the tomographic image within the region of the organ and classified as corresponding to the respective abnormal image pattern, and a total number of voxels in the region of the organ.

9. The computer-based diagnostic system of claim 1, wherein the tomographic image is of a chest of the patient; and the organ is a lung organ.

10. The computer-based diagnostic system of claim 9, wherein the deep machine learning unit is configured to provide a segmentation mask for all lung lobs of the lung organ during a preprocessing stage.

11. The computer-based diagnostic system of claim 10, wherein the set of abnormal image patterns includes image patterns corresponding to fibrosis, emphysema, honeycombing, ground glass opacity, reticular, cysts, consolidation and mosaic pattern attenuation.

12. The computer-based diagnostic system of claim 10, wherein the diagnostic result includes an indication of whether the region of the lung organ is affected by at least one of idiopathic pulmonary fibrosis (IFP) or related interstitial lung disease (ILD).

13. The computer-based diagnostic system of claim 9, wherein the set of abnormal image patterns includes image patterns corresponding to fibrosis, emphysema, honeycombing, ground glass opacity, reticular, cysts, consolidation and mosaic pattern attenuation.

14. The computer-based diagnostic system of claim 9, wherein the diagnostic result includes an indication of whether the region of the lung organ is affected by at least one of idiopathic pulmonary fibrosis (IFP) or interstitial lung disease (ILD).

15. A computer-based diagnostic method, comprising:
classifying, by a deep machine learning unit, a region of an organ of a patient as corresponding to one of a set of abnormal image patterns based on a tomographic image of the organ using a plurality of trained convolutional neural networks (CNNs) to obtain a classification result, the set of abnormal image patterns corresponding to diseased function tissue;
calculating a diagnostic result based on the classification result; and
outputting the diagnostic result via an interface, wherein
the plurality of trained CNNs correspond to a plurality of processing stages of the deep machine learning unit, the plurality of trained CNNs includes a first trained CNN corresponding to a localization stage among the plurality of processing stages and a second trained CNN corresponding to a classification stage among the plurality of processing stages, and
the classifying includes
delineating, by the first trained CNN, a plurality of respective regions of diseased functional tissue from regions of healthy tissue within a segment of the organ, the plurality of respective regions including the region, and
classifying, by the second trained CNN, each of the plurality of respective regions of diseased functional tissue as corresponding to a respective one of the set of abnormal image patterns.

16. A non-transitory computer-readable medium storing instructions that, when executed by processing circuitry, cause the processing circuitry to perform a computer-based diagnostic method, the method comprising:
classifying, by a deep machine learning unit, a region of an organ of a patient as corresponding to one of a set of abnormal image patterns based on a tomographic image of the organ using a plurality of trained convolutional neural networks (CNNs) to obtain a classification result, the set of abnormal image patterns corresponding to diseased function tissue;
calculating a diagnostic result based on the classification result; and
outputting the diagnostic result via an interface, wherein
the plurality of trained CNNs correspond to a plurality of processing stages of the deep machine learning unit, the plurality of trained CNNs includes a first trained CNN corresponding to a localization stage among the plurality of processing stages and a second trained CNN corresponding to a classification stage among the plurality of processing stages, and
the classifying includes
delineating, by the first trained CNN, a plurality of respective regions of diseased functional tissue from regions of healthy tissue within a segment of the organ, the plurality of respective regions including the region, and
classifying, by the second trained CNN, each of the plurality of respective regions of diseased functional tissue as corresponding to a respective one of the set of abnormal image patterns.

* * * * *